US006030348A

United States Patent [19]
Unger et al.

[11] Patent Number: 6,030,348
[45] Date of Patent: Feb. 29, 2000

[54] LEVELING DEVICE ESPECIALLY ADAPTED FOR USE IN APPARATUS FOR PERFORMING LIGHT BEAM GUIDED BIOPSIES AND THE LIKE

[75] Inventors: Evan Unger; Frederick Scott Pereles, both of Tucson, Ariz.

[73] Assignee: ImaRx Pharmaceutical Corp., Tucson, Ariz.

[21] Appl. No.: 08/789,524

[22] Filed: Jan. 27, 1997

[51] Int. Cl.$^7$ ..................................... A61B 10/00
[52] U.S. Cl. ........................................... 600/564
[58] Field of Search .................................. 600/564, 587

[56] References Cited

U.S. PATENT DOCUMENTS

| | | | |
|---|---|---|---|
| 4,296,329 | 10/1981 | Mirabella | 250/491 |
| 4,341,220 | 7/1982 | Perry | 128/630 |
| 4,385,397 | 5/1983 | Verro | 378/20 |
| 4,583,538 | 4/1986 | Onik et al. | 128/303 B |
| 4,592,352 | 6/1986 | Patil | 128/303 B |
| 4,651,732 | 3/1987 | Frederick | 128/303 R |
| 4,733,661 | 3/1988 | Palestrant | 128/303 B |
| 4,930,525 | 6/1990 | Palestrant | 128/898 |
| 5,031,203 | 7/1991 | Trecha | 378/205 |
| 5,047,036 | 9/1991 | Koutrouvelis | 606/130 |
| 5,230,623 | 7/1993 | Guthrie et al. | 600/587 |
| 5,316,014 | 5/1994 | Livingston | 128/754 |
| 5,320,111 | 6/1994 | Livingston | 128/754 |
| 5,494,034 | 2/1996 | Schlondorff et al. | 128/653.1 |
| 5,497,267 | 3/1996 | Ishikawa et al. | 359/390 |

OTHER PUBLICATIONS

Frederick, et al., "A Light–guidance System To Be Used for CT–guided Biopsy", Radiology, 1985.

Nagata, et al., "Laser Projection System for Radiotherapy and CT–Guided Biopsy", Technical Note, *Journal of Computer Assisted Tomography*, pp. 1046–1048, Nov./Dec. 1990.

Nishidai, et al., "CT Simulator: A New 3–D Planning and Simulating System for Radiotherapy: Part 1, Description of System," *I.J. Radiation Oncology Biol. Phys.*, vol. 18 No. 3, pp. 499–504, Mar. 1990.

(List continued on next page.)

*Primary Examiner*—Max Hindenburg
*Assistant Examiner*—Pamela L. Wingood
*Attorney, Agent, or Firm*—Woodcock Washburn Kurtz Mackiewicz & Norris LLP

[57] ABSTRACT

A leveling device capable of adjusting the inclination of a member, such as a vertical support post of a laser beam guidance apparatus for use in performing biopsies, in orthogonal first and second planes. The device has a fixed base plate upon which an intermediate tilt plate is rotatably supported so as to allow rotation of the intermediate tilt plate in the first plane. An upper tilt plate is rotatably supported on the intermediate tilt plate so as to allow rotation of the upper tilt plate in the second plane. A first adjusting screw provides adjustment of the rotation of the intermediate tilt plate in the first plane by imparting a force that counterbalances a spring force that also acts on the intermediate tilt plate. A second adjusting screw provides adjustment of the rotation of the upper tilt plate in the second plane by imparting a force that counterbalances a spring force that also acts on the upper tilt plate. The spring forces and the counterbalancing adjusting screw forces maintain the leveling device in the desired orientation.

17 Claims, 9 Drawing Sheets

OTHER PUBLICATIONS

Nagata, et al., "CT Simulator: A New 3–D Planning and Simulating System for Radiotherapy: Part 2, Clinical Application," *I.J. Radiation Oncology Biol. Phys.*, vol. 18 No. 3, pp. 505–513, Mar. 1990.

Wunschik, et al., "Stereoactic Biopsy Using Computed Tomography", *Journal of Computer Assisted Tomography*, vol. 8, No. 1, pp. 32–37, Feb. 1984.

Onik, et al., "CT Body Stereotaxis: An Aid for CT–Guided Biopsies", *AJR* 146, pp. 163–168, Jan. 1986.

Onik, et al., "CT–guided Aspirations for the Body: Comparison of Hand Guidance with Stereotaxis", *Radiology* vol. 166 No. 2, pp. 389–394, Feb. 1988.

Drummond, et al., "Deflection of spinal needles by the bevel", *Anaesthesia*, vol. 35, pp. 584–857, 1980.

E. Unger and F. Pereles, U.S. Application 08/356,150, "Apparatus for Performing Biopsies and the Like," filed Dec. 15, 1994.

LEVELING DEVICE ESPECIALLY ADAPTED FOR USE IN APPARATUS FOR PERFORMING LIGHT BEAM GUIDED BIOPSIES AND THE LIKE

FIELD OF THE INVENTION

The current invention is directed to a leveling device. More specifically, the current invention is directed to a leveling device for use in apparatus for performing light beam guided biopsies and other types of procedures in which it is necessary to adjust the inclination of a member.

BACKGROUND OF THE INVENTION

Imaging techniques such as computed tomography (CT) are often used to aid in directing the insertion of one or more probes into the patient's body during percutaneous biopsies and other similar procedures (e.g., hyperthermia probes, radiation seeds, etc.). In CT aided biopsies, for example, a scan is typically obtained to visualize the lesion to be biopsied. Using the image generated during the scan, the target site and the entry point on the patient's skin are selected and marked on the cathode ray tube (CRT) screen. The computer then calculates the distance and the angle of the insertion in order to reach the target site and displays the biopsy path on the screen.

The entry point is then marked on the patient's skin and the needle or probe is advanced into the patient's skin and tissues under free-hand control by the physician. Because of anatomy and overlying structures, the path selected for entry of the needle or probe is often not vertical but rather at an angle to the vertical. Often times a compound angle—that is, an angle with respect to the vertical in both the sagittal plane (i.e., the plane extending from head to toe) and the axial plane (i.e., the plane extending across the body from one side to the other) —must be used in order to avoid penetrating areas such as vital organs.

Although such procedures may be performed using a free-hand technique, it is difficult to ensure sufficient accuracy in orienting and maintaining the needle at the correct angle. The free-hand technique is even less precise and even more difficult when a compound angle is used. For example, in deep biopsies, even a few degrees deviation in angulation will result in a significant error in needle position. This can have undesirable consequences when the target lesion (e.g., tumor) is small and the path is close to surrounding vital structures, such as the aorta and nerves.

One solution is to direct a light or laser beam toward the target so that the physician can guide the insertion of the needle or probe along the line established by the beam. One such guidance apparatus is disclosed in the inventors' U.S. application Ser. No. 08/356,150, filed Dec. 15, 1994, entitled Apparatus for Performing Biopsies and the Like, which is hereby incorporated by reference in its entirety. In such apparatus, rotary stages are used to set the light beam angle in two orthogonal planes. For optimal use, such an apparatus requires the physician to level the structure supporting the rotary stages so that a setting of 0° on the rotary stages corresponds to the vertical direction.

It would be desirable to provide a leveling device that is especially adapted for use in an apparatus for performing light beam guided biopsies or other techniques in which it was necessary to level a portion of the structure.

SUMMARY OF THE INVENTION

It is an object of the current invention to provide a device for leveling a structure, especially an apparatus for performing light beam guided biopsies or similar procedures.

This and other objects of the invention are accomplished in a leveling device comprising (i) first and second plates, (ii) means for rotatably supporting the first plate for rotation within a first plane, (iii) means for rotatably supporting the second plate on the first plate so as to permit rotation of the second plate within a second plane perpendicular to the first plane, (iv) means for applying a first force tending to rotate the first plate in a clockwise direction within the first plane, (v) means for applying a second force tending to rotate the first plate in a counter-clockwise direction within the first plane, (vi) means for applying a third force tending to rotate the second plate in a clockwise direction within the second plane, and (vii) means for applying a fourth force tending to rotate the second plate in a counter-clockwise direction within the second plane.

In one embodiment, the leveling device is incorporated into an apparatus for generating a beam of light for use in guiding the entry of a probe into a patient's body. In this application, the light beam generating apparatus comprises (i) means for generating a beam of light, (ii) a support structure for supporting the light beam generating means, (iii) means for adjusting the inclination of the support structure in first and second orthogonal planes. The inclination adjusting means includes a first plate, a second plate rotatably mounted on the first plate for rotation within the first plane, and a third plate rotatably mounted on the second plate for rotation with the second plane. The support structure is mounted on the third plate.

DESCRIPTION OF THE PREFERRED EMBODIMENT

Figure 1:
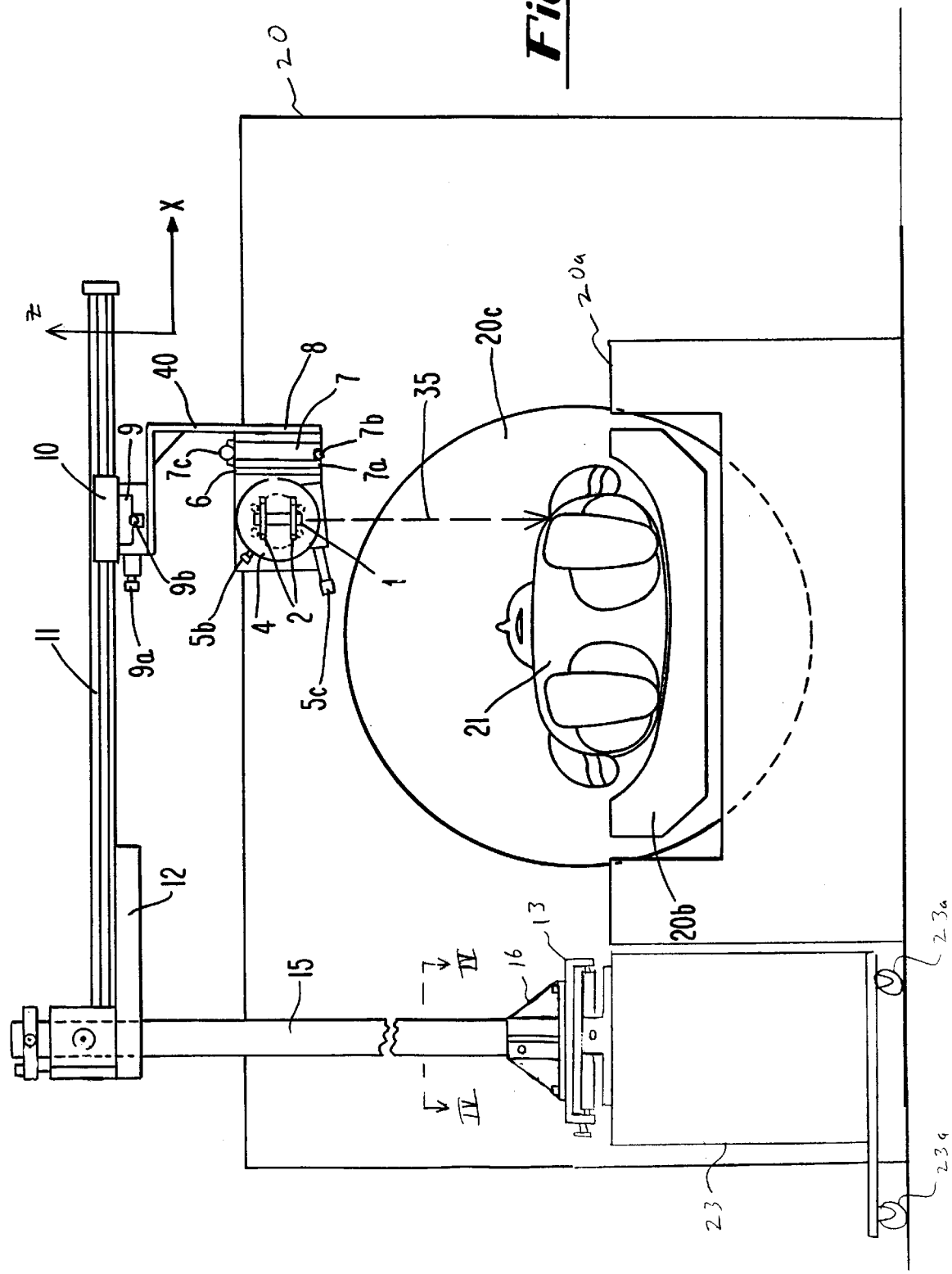
FIG. 1 is an end view of the light beam supporting and directing apparatus, mounted next to a CT table, utilizing the leveling device according to the current invention.

There is shown in FIG. 1 a laser beam guidance apparatus for performing biopsies and the like utilizing the leveling device according to the current invention. The system for performing light beam guided biopsies includes a CT machine 20, a CT table 20a, a CT couch 20b and a gantry 20c. A Cartesian coordinate system is shown, with the z-direction being vertical, the x-direction being transverse to the body of a patient lying on the couch 20b, and the y-direction extending longitudinally along the patient from head to toe. Thus, the X-Z plane defines an axial plane and the Y-Z plane defines a sagittal plane.

Figure 7:
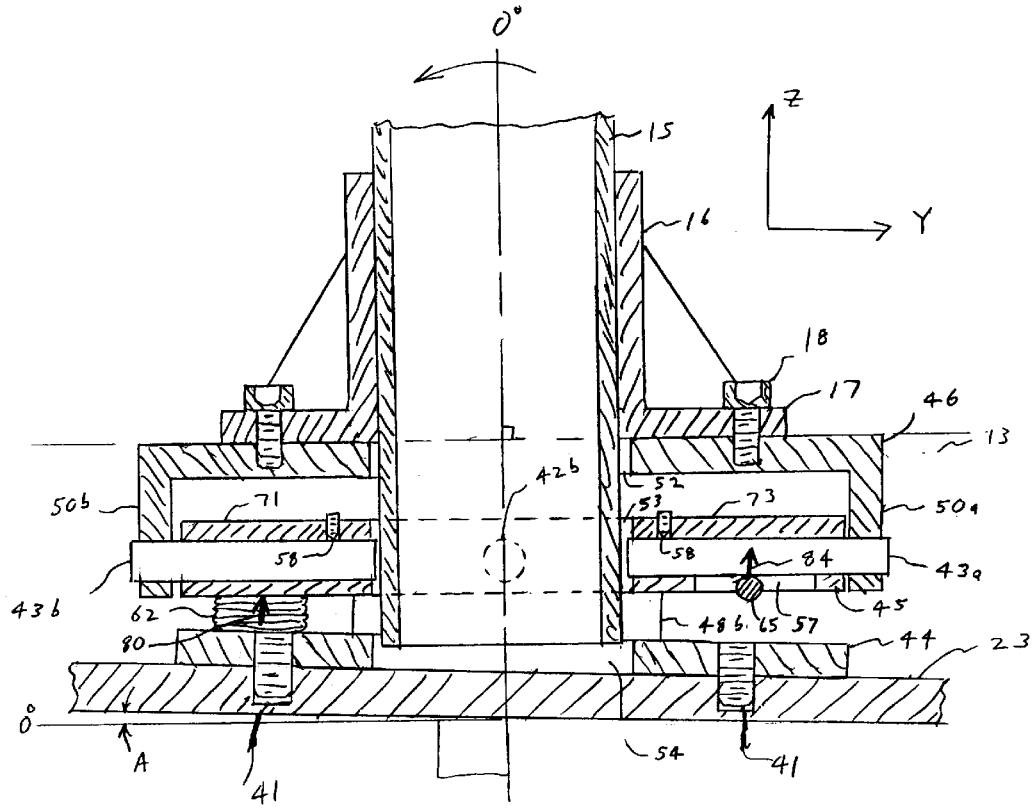
FIG. 7 is a cross-section taken along line VII—VII shown in FIG. 4 illustrating correction of orientation in the Y-Z plane.

As shown in FIG. 1, the light beam guidance apparatus is positioned next to the side of the CT table 20a using a portable floor stand 23. As shown in FIG. 7, a base plate 44 of the leveling device 13 according to the current invention, discussed in detail below, is secured via screws 41 to the top plate of the portable floor stand 23. The stand 23 has locking casters 23a, such as those available from Darcor Inc. of Brea, Calif. (model OU-BC5-XSRB) or a cooperative floor jack system, such as that disclosed in the aforementioned U.S. application Ser. No. 08/356,150, that allow it to be locked into position so that it can no longer move during the procedure unless repositioning is desired. Although as shown in FIG. 1, the light beam guidance apparatus is attached to a portable floor stand 23, the leveling device of the current invention is also applicable to other arrangements, such as those in which the light beam guidance apparatus is attached to a y-direction track attached to the CT table 20a, as shown in the aforementioned U.S. application Ser. No. 08/356,150, or to the ceiling.

A vertical support post 15 is mounted on the leveling device 13 by means of a collar 16 that clamps around the support post. The base plate 17 of the collar 16 is attached to an upper plate 46 of the leveling device 13 by means of screws 18, as shown in FIG. 7. Consequently, as discussed in detail below, the leveling device 13 allows the inclination of the support post 15 to be adjusted.

An x-direction rail 11 is slidably mounted on the vertical support post 15 by means of a rigid right angle clamp 12 that clamps to the vertical support post. A suitable clamp is model M-300-P available from Newport Corp., Irvine, Calif. A laser beam supporting structure 40 is slidably mounted on the rail 11. A laser 1 installed on support structure 40 generates a beam of light 35 that can be aimed at a patient 21, as discussed further below, and used to guide the path of a biopsy probe.

Figure 2:
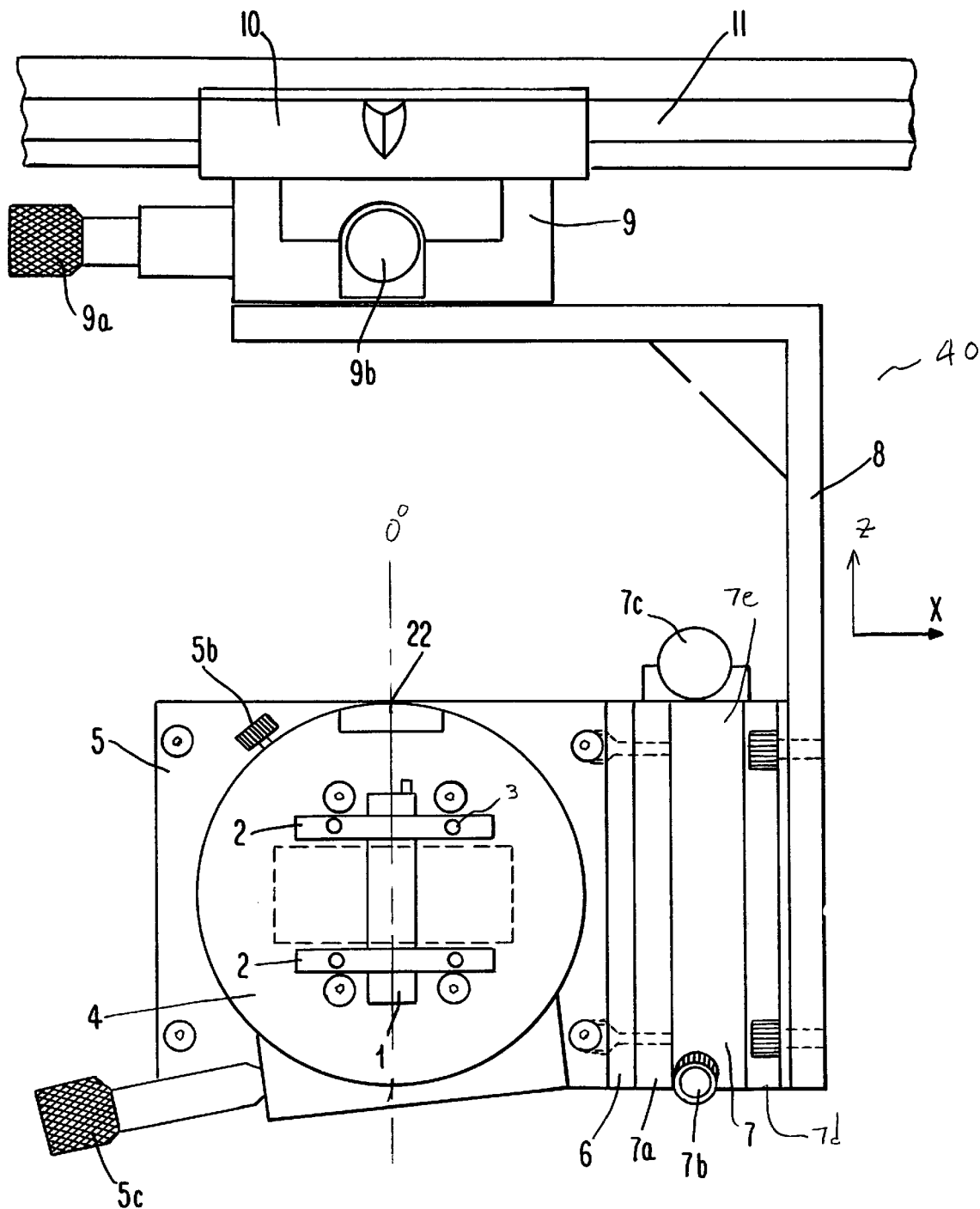
FIG. 2 is an end view of the laser mounting block assembly and support structure portion of the apparatus shown in FIG. 1.
Figure 3:
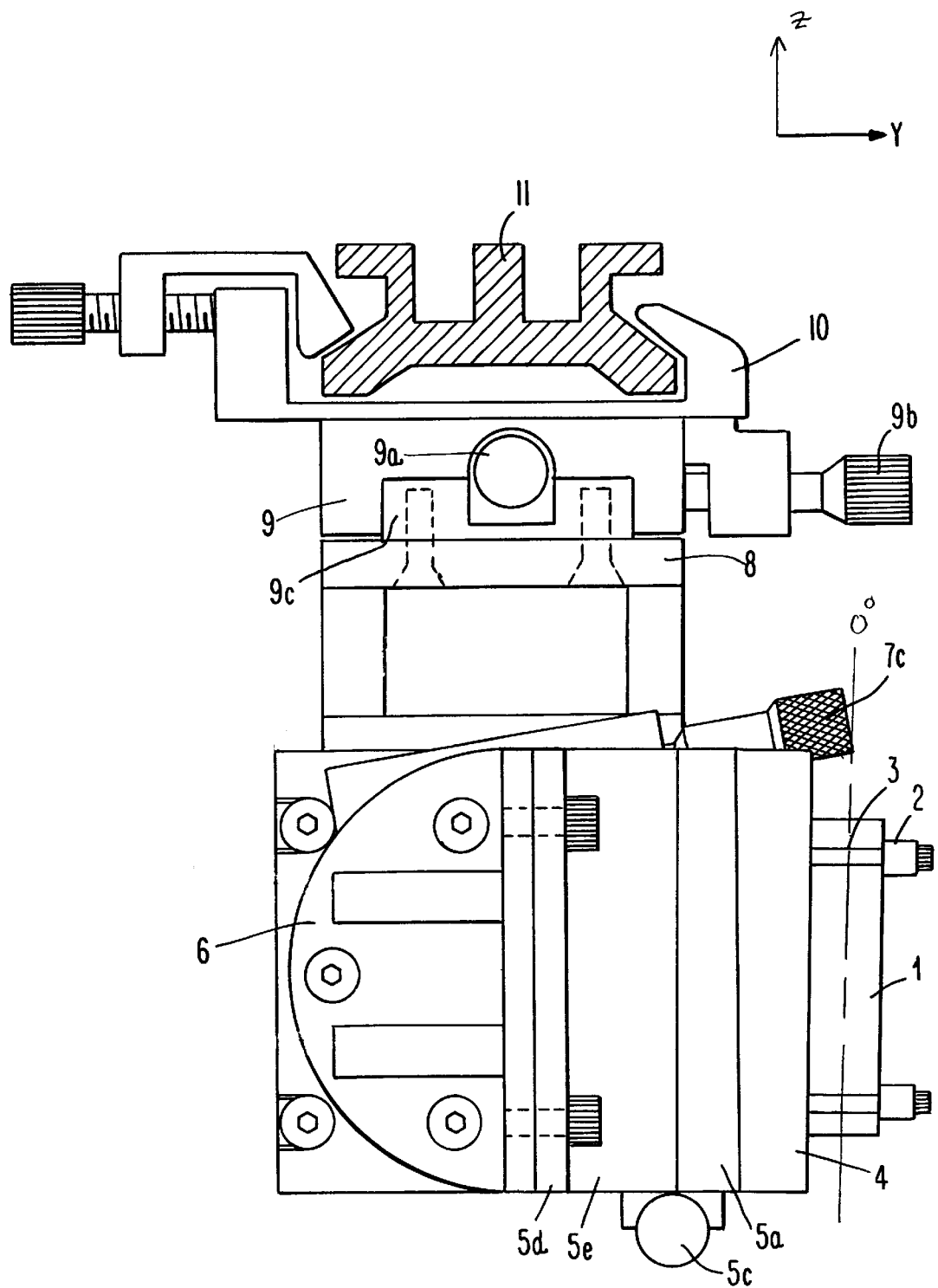
FIG. 3 is a side view of the laser mounting block assembly and support structure shown in FIG. 2.
Figure 4:
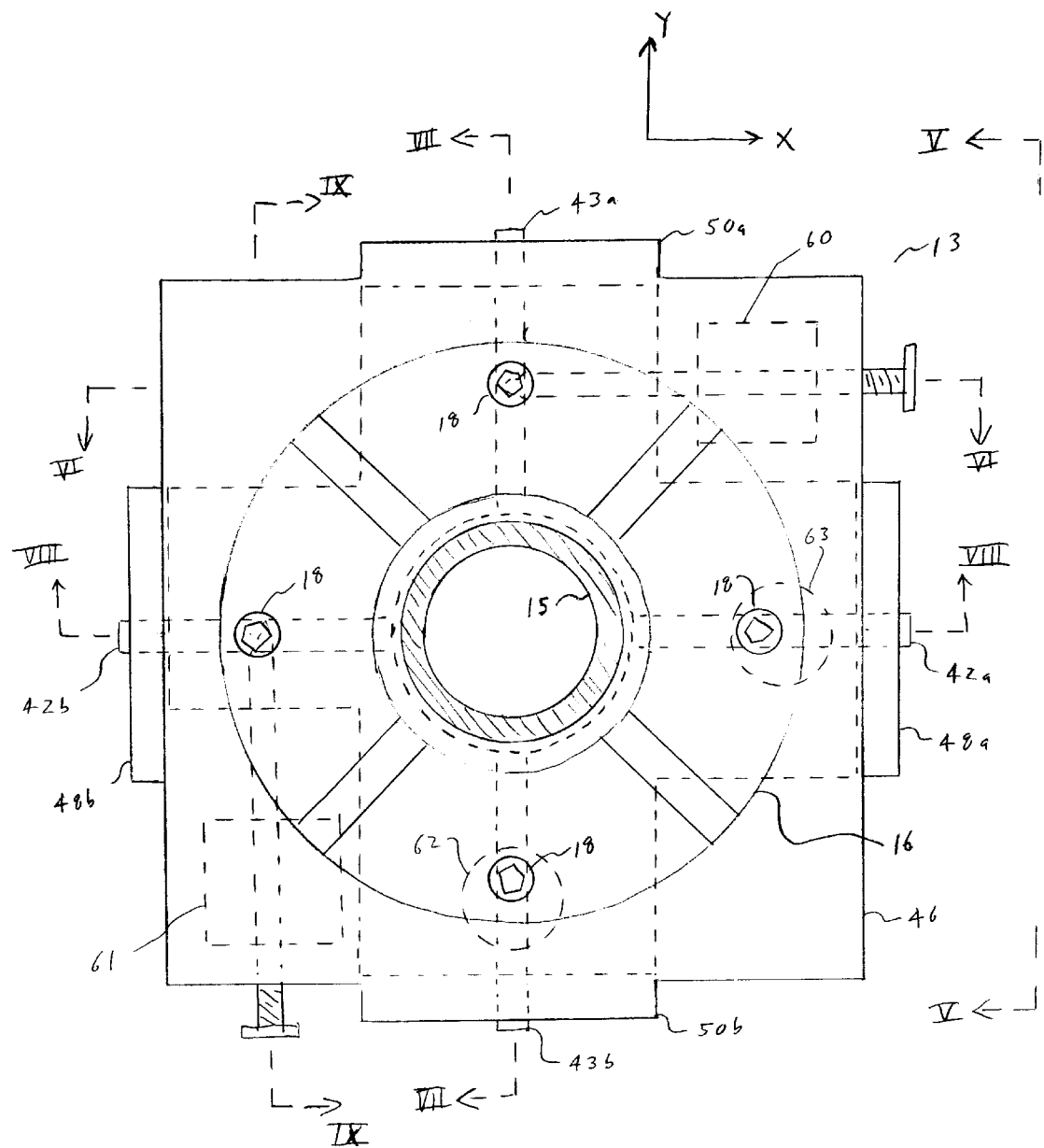
FIG. 4 is cross-section through the vertical support post taken along line IV—IV shown in FIG. 1.

As shown in FIGS. 2 and 3, the laser 1, which may be of the helium neon diode type, is secured within a groove formed in a plastic mounting block 4, such as a delrin block, using two tie down bars 2 that are attached to the mounting block 4 by screws 3. This arrangement ensures that the laser 1 will maintain its orientation with respect to the mounting block 4. Suitable lasers include model CPM 01-670-A-C available from Power Technology Inc. of Little Rock, Ark.

Figure 2A:
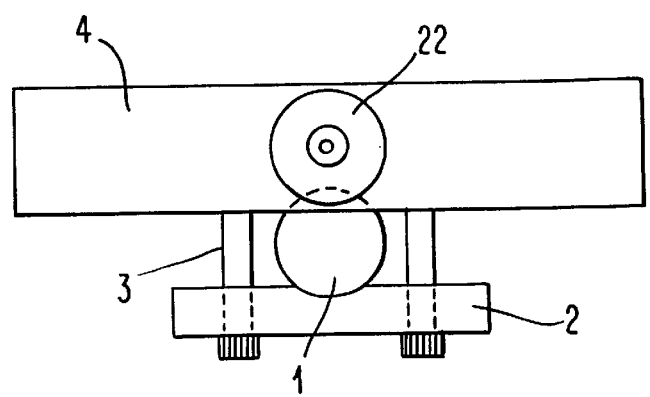
FIG. 2a is a plan view of the laser mounting block assembly shown in FIG. 2.

Preferably, a level indicating device 22, such as a bull's eye leveling bubble, is incorporated into the mounting block 4, as shown in FIGS. 2 and 2a. When used in conjunction with the leveling device 13 according to the current invention, the leveling indicating device 22 allows the user to accurately orient the laser in the dead vertical position (i.e., a 0° angle with respect to the z-direction in both the X-Z and Y-Z planes) before setting the beam angle based on the CT image. As a result of closely coupling the level indicating device 22 to the laser 1, by securing both directly onto the same mounting block 4, the user can ensure that the beam angle set on the rotary stages, discussed below, will accurately reflect the angle of the laser with respect to the z-direction in both the X-Z and Y-Z planes.

As shown in FIGS. 2 and 3, the laser supporting structure 40 includes two rotary stages 5 and 7 oriented perpendicularly to each other. Each rotary stage 5 and 7 is comprised of a mounting plate 5d and 7d, a fixed ring 5e and 7e, a rotatable ring 5a and 7a coupled to the fixed ring, a locking screw 5b and 7b, and a fine adjustment caliper 5c and 7c. A suitable rotary stage is model M-481-A, available from Newport Corp. of Irvine, Calif. The rotary stages 5 and 7 are fixed at a right angle with respect to each other by aluminum brackets 6 and 8. The laser mounting block 4 is itself mounted on the rotatable ring 5a of the rotary stage 5. The base plate 5d of the rotary stage 5 is secured to the bracket 6, which is secured to the rotatable ring 7a of the rotary stage 7. The base plate 7e of the rotary stage 7 is secured to the bracket 8.

The rotary stages 5 and 7 allow adjustment of the beam angle in two mutually perpendicular vertical planes. The rotary stage 5 allows adjustment of the laser beam 35 angle within the X-Z plane, while the rotary stage 7 allows adjustment of the laser beam angle within the Y-Z plane. Thus, by properly adjusting the rotary stages 5 and 7, the laser beam 35 can be set to a compound angle with respect to the z-direction. Alternatively, if, for example, an angle is required in only the Y-Z plane (i.e., the sagittal plane), the rotary stage 5 can be set to 0°.

As also shown in FIGS. 2 and 3, the bracket 8 is suspended from a bidirectional translational stage 9. The translational stage 9 comprises a support plate 9c to which the bracket 8 is attached and that is slidably mounted within the translational stage 9 so as to be free to move in both the x and y directions. A caliper 9b moves the support plate 9c in the y direction and a caliper 9a moves the support plate 9c in the x direction. A suitable translational stage is model 460A-XY available from Newport Corp. The translational stage 9 permits fine translational adjustment in the x and y directions in a horizontal plane.

The translational stage 9 is attached to an optical rail carrier 10. A suitable rail carrier is model 07 OCN 503 available from Melles Griot of Irvine, Calif. The carrier 10 is free to move along the horizontal rail 11 that extends perpendicularly to the support post 15. A suitable rail is model 07 ORN 005 available from Melles Griot. Preferably, rail 11 has a metric ruled side with millimeter markings for translational distance adjustment. Movement along the rail 11 provides rapid gross adjustment in the x direction when the rail is perpendicular to the CT table 20a.

The apparatus is used as follows: First, the patient is placed onto the scanner table 20b and the necessary scans are taken of the relevant area, as discussed in aforementioned U.S. application Ser. No. 08/356,150. After the relevant scans are obtained, a needle path is chosen. A cursor is used to mark the entry site and the target site on the CRT monitor. The needle insertion depth and the angle of the path, with respect to the z direction, projected onto the X-Z and Y-Z planes are then calculated by the computer and the needle path is displayed on the CRT monitor.

The laser support structure 40 is moved into the approximate desired position in the x and y directions by movement of the portable stand 23 and in the z direction by movement of the rail 11 along the vertical post 15. When the stand 23 is in the proper position, it is clamped into the locked position via the locking swivel casters 23a. The portable floor stand 23 can be positioned anywhere along the CT table on either side or even at either end of the CT table, if needed, thereby providing maximum flexibility.

Once the floor stand is locked in place, the leveling device 13 is used to adjust the inclination of the support post 15, as discussed further below, so that the bubble in bull's eye level 22 is centered. This ensures that the laser beam support structure 40 is oriented so that an angle of 0° on the settings of the rotary stages 5 and 7 will result in a beam 35 that is oriented exactly in the vertical direction in both the X-Z and Y-Z planes, thereby providing a proper frame of reference for setting the beam angle. Once the laser beam support structure 40 is properly oriented, the rotary stage 5 is then set to the calculated angle in the X-Z plane and the rotary stage 7 is set to the desired angle in the Y-Z plane.

Gross adjustment in the x direction is then accomplished by sliding the carrier 10 along the horizontal rail 11, as previously discussed. Fine adjustment along the x and y directions is then achieved, using the bidirectional translational stage 9, until the laser beam 35 strikes the patient's skin at the pre-determined entry location.

A needle (such as a B-D spinal needle available from Becton Dickinson Co. of Franklin Lakes, N.J. or the probe discussed in the aforementioned application Ser. No. 08/356, 150) is then placed such that the end of the needle touches the patient's skin at the same point as the laser beam. The hub of the needle is aligned such that the needle is now directly centered in the laser beam and therefore parallel to the laser beam as well. Using a free-hand technique, the needle is advanced into the patient to a predetermined depth while keeping the laser light centered onto the mid-point of the posterior surface of the needle's hub to ensure that the needle follows the desired path.

For use in CT, the components of the device, especially stages 5, 7, 9, rail 11, and support post 15, are preferably made of light weight steel, aluminum, fiberglass, carbon fiber, or composite plastics such as delrin. For use in Magnetic Resonance Imaging (MR) techniques, the device should be made of MR compatible materials and the use of ferromagnetic materials should be avoided. Preferred materials for constructing the device would include high nickel steel, aluminum, carbon fiber and fiber glass.

Figure 5:
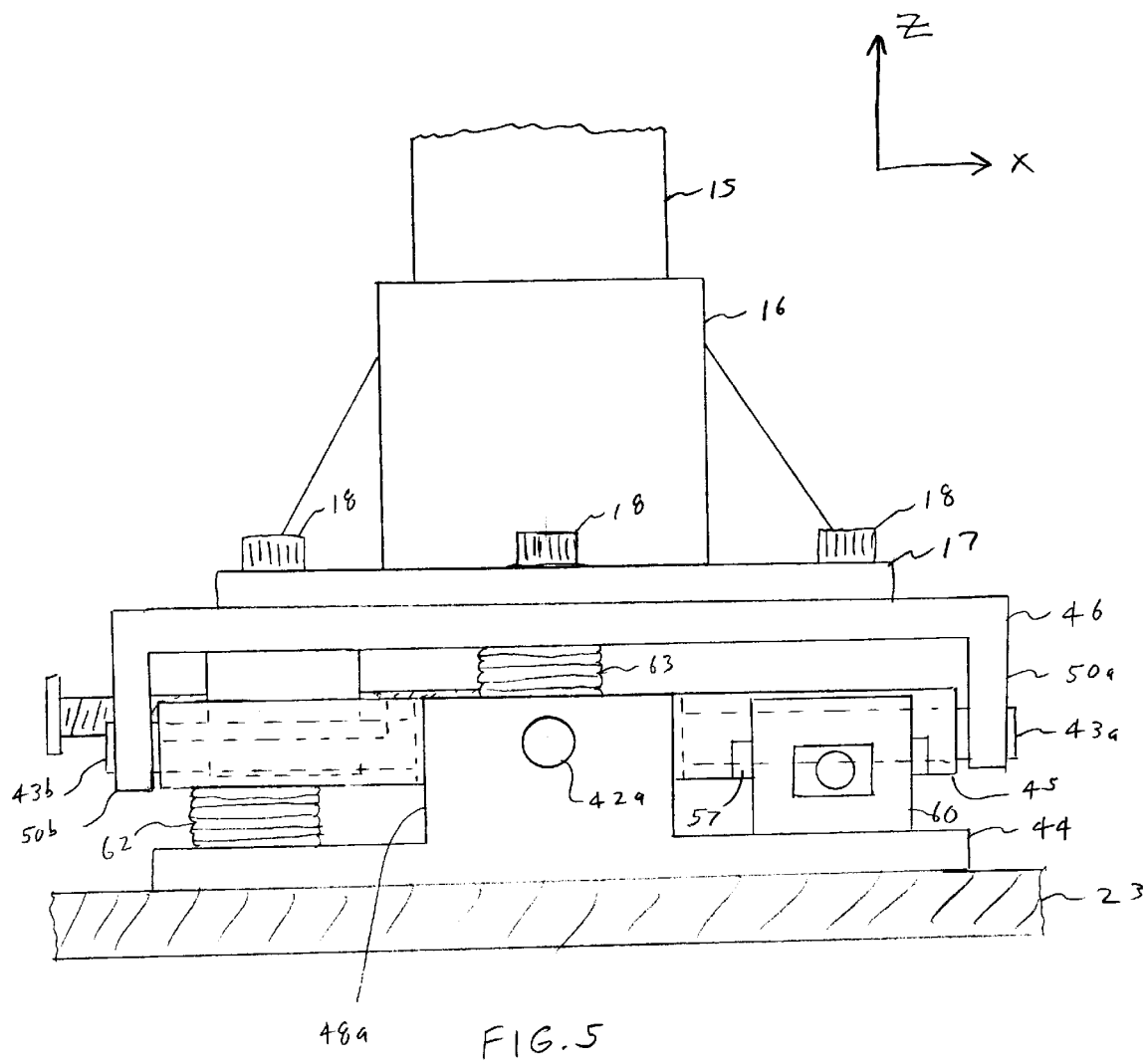
FIG. 5 is a detailed view of the leveling device portion of the apparatus shown in FIG. 1 taken along line V—V shown in FIG. 4.
Figure 8:
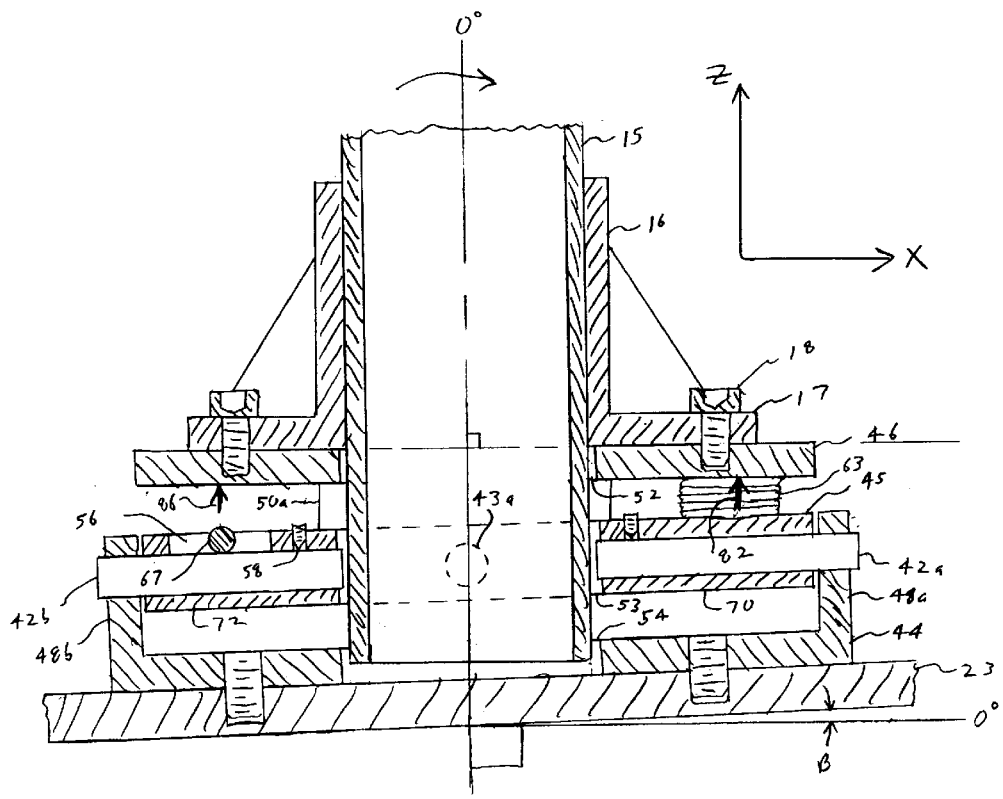
FIG. 8 is a cross-section taken along line VIII—VIII shown in FIG. 4 illustrating correction of orientation in the X-Z plane.

The structure and operation of the leveling device 13, shown in FIGS. 4–10, will now be discussed in detail. As shown in FIG. 5, the leveling device 13 is comprised of a base plate 44, an upper tilt plate 46, and an intermediate tilt plate 45 disposed between the base plate and the upper tilt plate. As discussed further below, the intermediate tilt plate 45 provides for rotation, and therefore adjustment of the inclination of the support post 15, in the Y-Z plane, as shown in FIG. 7. The upper tilt plate 46 provides for rotation, and therefore adjustment of inclination of the support post, in the X-Z plane, as shown in FIG. 8.

Figure 10:
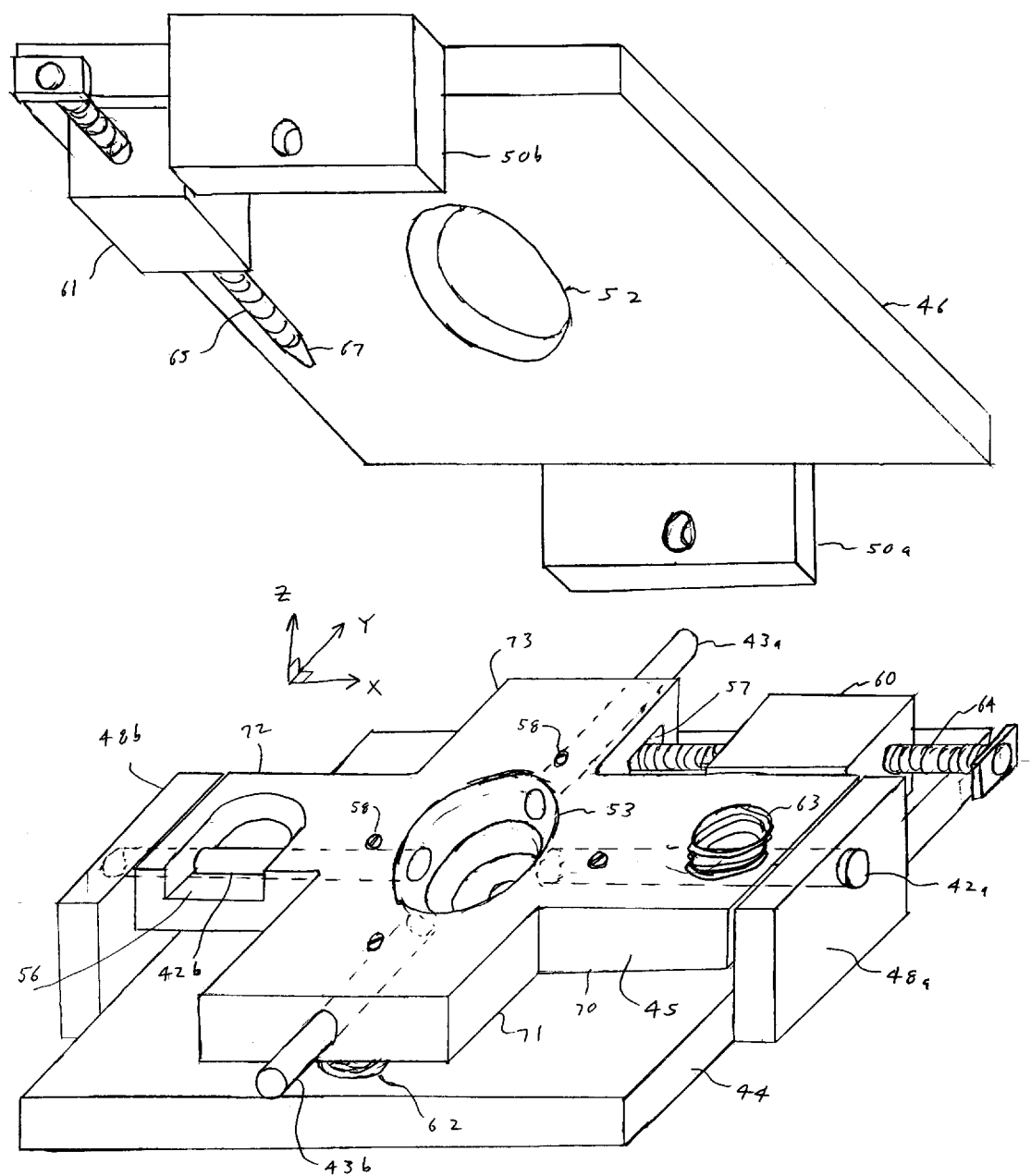
FIG. 10 is an exploded isometric view of the leveling device of the current invention.

As shown best in FIG. 10, the base plate 44 and the upper tilt plate 46 are preferably of identical construction and comprise flat members in which centrally disposed holes 52 and 54, respectively, are formed. Although, as shown, the flat members of the base plate 44 and upper tilt plate 46 are square, other shapes could also be utilized, such as hexagonal. Pairs of flanges 48 and 50 project from opposing sides of the flat members, threaded blocks 60 and 61 are attached to surfaces of the flat members, and adjusting screws 65 and 64 extend through the threaded blocks.

As also shown best in FIG. 10, the intermediate tilt plate 45 has an approximately cross shape and a centrally disposed hole 53. Bearing pins 42a, 42b, 43a and 43b extend through holes in each of the four arms 70–73 of the cross-shape. Set screws 58 prevent the intermediate tilt plate 45 from rotating about the bearing pins. Bearing pins 42a and 42b are rotatably mounted in bearing holes formed in the flanges 48a and 48b that project upwardly on opposing sides the base plate 44. The bearing pins 42a and 42b allow the intermediate tilt plate 45 to rotate in the Y-Z plane. Similarly bearing pins 43a and 43b are rotatably mounted bearing holes formed in flanges 50a and 50b that project downwardly on opposing sides the upper tilt plate 46. The bearing pins 43a and 43b allow the upper tilt plate 46 to rotate in the X-Z plane.

As shown in FIG. 7, hole 53 in the intermediate tilt plate 53 is aligned with the holes 52 and 54 formed in base plate 44 and the upper tilt plate 46, respectively, thereby allowing the end of the support post 15 to extend through the plates.

Figure 9:
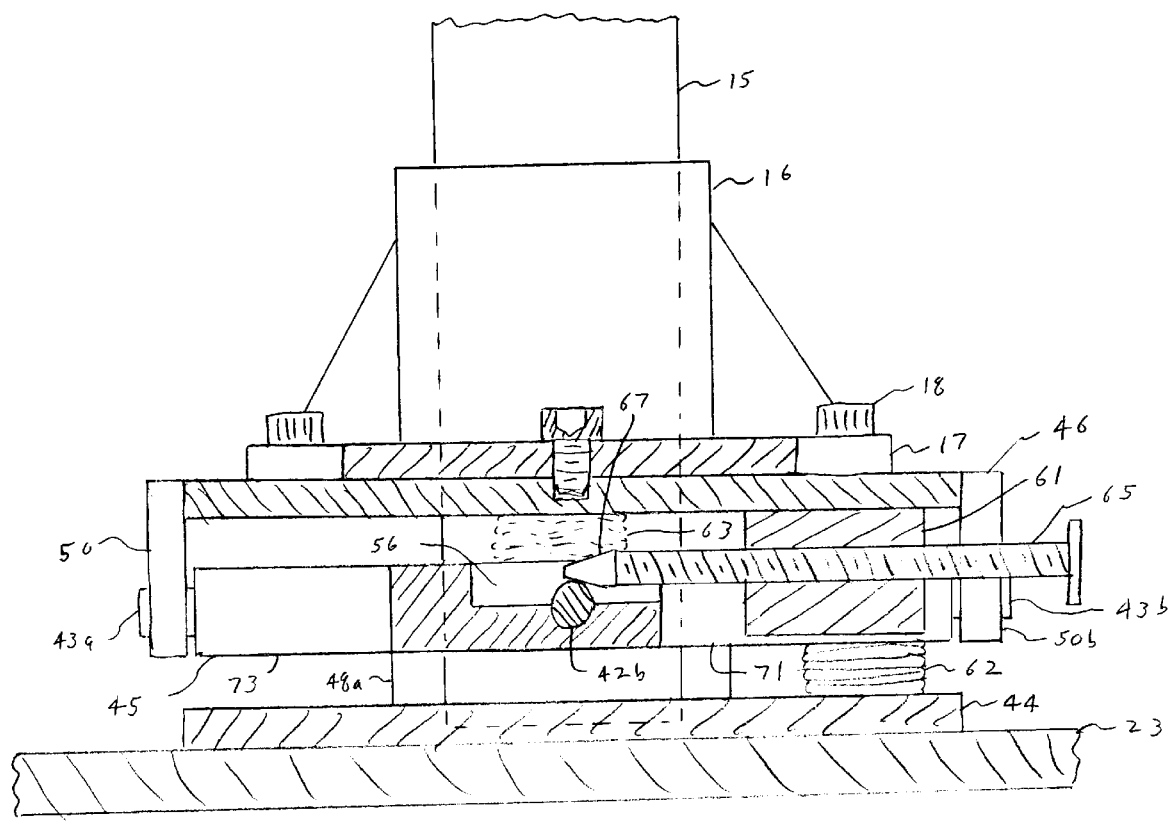
FIG. 9 is a cross-section taken along line IX—IX shown in FIG. 4.

As shown best in FIGS. 9 and 10, an approximately U-shaped groove 56 is formed in upper surface of the arm 72 of the intermediate tilt plate 45, exposing a portion of the bearing pin 42b. The block 61, in which a threaded hole is formed, is attached to the lower surface of the upper tilt plate 46. A threaded adjusting screw 65, having a conical point 67, extends through the hole in the thread block 61 and projects into the groove 56 so that the conical point contacts the portion of the bearing pin 42b extending through the groove.

Figure 6:
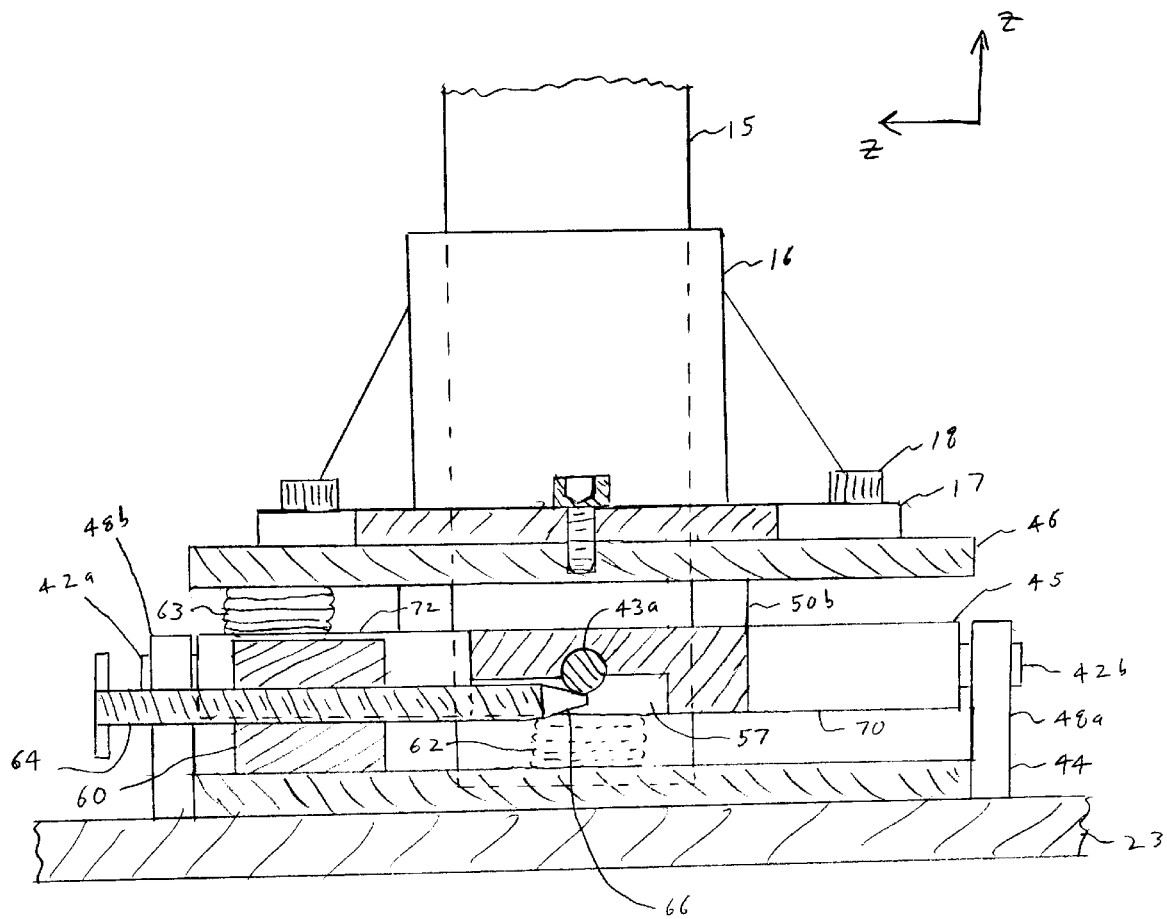
FIG. 6 is a cross-section taken along line VI—VI shown in FIG. 4.

As shown best in FIGS. 6 and 10, an approximately U-shaped groove 57, similar to U-shaped groove 56 in the upper surface of arm 72, is formed in lower surface of the arm 73 of the intermediate tilt plate 45, exposing a portion of the bearing pin 43a. The thread block 60, which is similar to the thread block 61, is attached to the upper surface of the base plate 44. A threaded adjusting screw 64, having a conical point 66, extends through the hole in the thread block 60 and projects into the groove 57 so that the conical point contacts the portion of the bearing pin 43a extending though the groove.

As shown best in FIGS. 7 and 10, a helical compression spring 62 is disposed between the base plate 44 and the lower surface of arm 71 of the intermediate tilt plate 45. The spring 62 exerts an upward force 80 that is proportional to the amount by which the spring is compressed and, therefore, to the amount of rotation of the intermediate tilt plate in the Y-Z plane. The force 80 urges the intermediate tilt plate 45 to rotate in the clockwise direction, as viewed in FIG. 7, within the Y-Z plane.

As seen in FIGS. 6 and 7, as the adjusting screw 64 is threaded into the thread block 60, its conical tip 65 comes into contact with the bearing pin 43a. As a result of the sloping conical surface of the tip 65, as the adjusting screw is threaded in, it exerts a progressively increasing upward force 84 against the bearing pin 43a that counterbalances force 62 and urges the intermediate tilt plate 45 to rotate in the counter-clockwise direction within the Y-Z plane. Threading the adjusting screw 64 out reduces the force 84, causing the spring force 80 to rotate the intermediate tilt plate 45 in the clockwise direction. Thus, by threading the adjusting screw 64 into or out of the thread block 60, the angular orientation of the intermediate tilt plate 45 within the Y-Z plane can be adjusted to any angle desired, within the range of motion permitted by the clearance between the intermediate tilt plate and the base plate 44. The counterbalancing forces 80 and 84 will ensure that the level device 13 maintains the desired angular setting.

Note that the upper tilt plate 46 cannot rotate in the Y-Z plane, since it is supported by the bearing pins 43a and 43b, which are oriented in the Y direction. Therefore, with respect to rotation in the Y-Z plane, the upper and intermediate tilt plates 46 and 45 rotate as a unit. Consequently, if, for example, as a result of an out-of-level floor, the top plate of the portable support stand 23 is tilted at an angle A to true horizontal in the Y-Z plane, as shown in FIG. 7 (horizontal being indicated by 0° horizontal line in FIG. 7), the adjusting screw 64 can be utilized to level the upper tilt plate 46 in the Y-Z plane. This leveling adjusts the inclination of the support post 15 as necessary to properly orient the laser beam support structure 40 in the Y-Z plane, for example, based on the reading of the bull's eye level 22.

As shown best in FIGS. 8 and 10, a helical compression spring 63 is disposed between the upper surface of arm 70 of the intermediate tilt plate 45 and the upper tilt plate 46. The spring 63 exerts a upward force 82 that is proportional to the amount by which the spring is compressed and, therefore, to the amount of rotation of the upper tilt plate in the X-Z plane. The force 63 urges the upper tilt plate 46 to rotate in the counter-clockwise direction, as viewed in FIG. 8, within the X-Z plane.

As shown in FIGS. 8 and 9, as the adjusting screw 65 is threaded into the thread block 61 its conical tip 67 exerts a progressively increasing downward force against the bearing pin 42b in a manner similar to that discussed above with respect to adjusting screw 64. The intermediate tilt plate 45 cannot rotate in the X-Z plane since it is support by the bearing pins 42a and 42b, which are oriented in the X direction. Consequently, the contact between the adjusting screw 65 and the bearing pin 42b creates a upward reaction force 86 that acts through the thread block 61 to urge the upper tilt plate 46 to rotate in the clockwise direction so as to counterbalance the force 82. Thus, by threading the adjusting screw 65 into or out of the thread block 61, the angular orientation of the upper tilt plate 46 within the X-Z plane can be adjusted to any angle desired, within the range of motion permitted by the clearance between the upper tilt plate 46 and the intermediate tilt plate 45. The counterbalancing forces 82 and 86 will ensure that the level device 13 maintains the desired angular setting.

Consequently, if, for example, as a result of an out-of-level floor, the top plate of the portable support stand 23 is tilted at an angle B to true horizontal in the X-Z plane as shown in FIG. 8, the adjusting screw 65 can be utilized to level the upper tilt plate 46 in the X-Z plane and, therefore adjust the inclination of the support post 15 as necessary to properly orient the laser beam support structure 40 in the X-Z plane, again, for example, based on the reading of the bull's eye level 22.

As can seen the leveling device 13 allows the orientation of the support post 15 to be readily and accurately set to a given inclination and holds that setting throughout the procedure.

Although the present invention has been discussed with reference to a laser beam guidance apparatus for use in CT aided biopsies, the device is also applicable for use in procedures other than biopsies, as well as procedures aided by other means, such magnetic resonance imaging, ultrasound, and X-ray. Moreover, although the invention has been discussed with reference to the guidance of a probe via a light beam, the invention is also applicable for use with mechanical guidance devices, in which case, the leveling device can be used to adjust the inclination of the mechanical guide. Although the invention has been disclosed with reference to a biopsy probe, it is also applicable for use with other types of probes or devices, including interventional probes or devices such as needles, drills, and saws, as well as RF probes and therapeutic ultrasound, in which it is desired to level or otherwise adjust the inclination of a member. Consequently, the present invention may be embodied in other specific forms without departing from the spirit or essential attributes thereof and, accordingly, reference should be made to the appended claims, rather than to the foregoing specification, as indicating the scope of the invention.

What is claimed:

1. An apparatus for orienting a guidance device with respect to a patient's body, comprising:
   a) a support structure for supporting said guidance device, said support structure having an angular position;
   b) means for permitting said support structure to rotate within a range of angular motion in first and second orthogonal planes so as to vary said angular position thereof, said rotation permitting means comprising (i) a first member, (ii) a second member rotatably mounted on said first member for rotation within said first plane, (iii) a third member rotatably mounted on said second member for rotation within said second plane, said support structure coupled to said third member;
   c) first position adjusting means for setting an angular position of said second member by rotating said second member in a first direction within said first plane; and
   d) first force generating means for maintaining said angular position of said second member by generating a force tending to rotate said second member within said first plane in a direction opposite to said first direction, said first force generating means generating said force in response to said rotation of said second member in said first direction,
   whereby said angular position of said support structure may be accurately adjusted and maintained at any angular position within said range of angular motion permitted by said rotation permitting means.

2. The apparatus according to claim 1, wherein said first position adjusting means comprises a threaded member.

3. The apparatus according to claim 1, wherein said support structure comprises a support post to which said guidance device is coupled.

4. The apparatus according to claim 1, wherein said support structure comprises means for directing a laser.

5. The apparatus according to claim 1, wherein said first force generating means has means for generating a force having a magnitude proportional to the amount of rotation of said second member in said first direction within said first plane.

6. The apparatus according to claim 1, wherein said first force generating means comprises a spring.

7. The apparatus according to claim 1, further comprising:
   e) second position adjusting means for setting an angular position of said third member by rotating said third member in a first direction within said second plane; and
   f) second force generating means for maintaining said angular position of said third member by generating a force tending to rotate said third member within said second plane in a direction opposite to said first direction, said second force generating means generating said force in response to said rotation of said third member in said first direction.

8. The apparatus according to claim 7, wherein said second position adjusting means comprises a threaded member.

9. The apparatus according to claim 7, wherein said second force generating means has means for generating a force having a magnitude proportional to the amount of rotation of said third member in said first direction within said second plane.

10. The apparatus according to claim 7, wherein said second force generating means comprises a spring.

11. An apparatus for orienting a guidance device with respect to a patient's body, comprising:

a) a support structure for supporting said guidance device;

b) means for adjusting the inclination of said support structure in first and second orthogonal planes, said inclination adjusting means including (i) a first plate, (ii) a second plate rotatably mounted on said first plate for rotation within said first plane, (iii) a third plate rotatably mounted on said second plate for rotation within said second plane, said support structure mounted on said third plate;

c) means for applying a first force tending to rotate said second plate in a first direction within said first plane;

d) means for applying a second force tending to rotate said second plate in a second direction opposite to said first direction within said first plane, wherein said second force applying means has means for generating a force having a magnitude proportional to the amount of rotation of said second plate in said second direction.

12. An apparatus for orienting a guidance device with respect to a patient's body, comprising:

a) a support structure for supporting said guidance device;

b) means for adjusting the inclination of said support structure in first and second orthogonal planes, said inclination adjusting means including (i) a first plate, (ii) a second plate rotatably mounted on said first plate for rotation within said first plane, (iii) a third plate rotatably mounted on said second plate for rotation within said second plane, said support structure mounted on said third plate;

c) means for applying a first force tending to rotate said second plate in a first direction within said first plane;

d) means for applying a second force tending to rotate said second plate in a second direction opposite to said first direction within said first plane, wherein said second force applying means comprises a spring.

13. An apparatus for orienting a guidance device with respect to a patient's body, comprising:

a) a support structure for supporting said guidance device;

b) means for adjusting the inclination of said support structure in first and second orthogonal planes, said inclination adjusting means including (i) a first plate, (ii) a second plate rotatably mounted on said first plate for rotation within said first plane, (iii) a third plate rotatably mounted on said second plate for rotation within said second plane, said support structure mounted on said third plate;

c) means for applying a first force tending to rotate said second plate in a first direction within said first plane;

d) means for applying a second force tending to rotate said second plate in a second direction opposite to said first direction within said first plane;

e) means for applying a third force tending to rotate said third plate in a third direction within said second plane;

f) means for applying a fourth force tending to rotate said third plate in a fourth direction opposite to said third direction within said second plane, wherein said fourth force applying means has means for generating a force having a magnitude proportional to the amount of rotation of said third plate in said fourth direction.

14. An apparatus for orienting a guidance device with respect to a patient's body, comprising:

a) a support structure for supporting said guidance device;

b) means for adjusting the inclination of said support structure in first and second orthogonal planes, said inclination adjusting means including (i) a first plate, (ii) a second plate rotatably mounted on said first plate for rotation within said first plane, (iii) a third plate rotatably mounted on said second plate for rotation within said second plane, said support structure mounted on said third plate;

c) means for applying a first force tending to rotate said second plate in a first direction within said first plane;

d) means for applying a second force tending to rotate said second plate in a second direction opposite to said first direction within said first plane;

e) means for applying a third force tending to rotate said third plate in a third direction within said second plane;

f) means for applying a fourth force tending to rotate said third plate in a fourth direction opposite to said third direction within said second plane, wherein said fourth force applying means comprises a spring.

15. An apparatus for guiding the entry of a probe into a patient's body using a light beam, comprising:

a) means for generating a beam of light;

b) a support structure for supporting said light beam generating means, said support structure having an angular position;

c) means for permitting said support structure to rotate within a range of angular motion in first and second orthogonal planes so as to vary said angular position thereof, said rotation permitting means comprising (i) a first member, (ii) a second member rotatably mounted on said first member for rotation within said first plane, (iii) a third member rotatably mounted on said second member for rotation within said second plane, said support structure mounted on said third member;

d) position adjusting means for setting an angular position of said second member by rotating said second member in a first direction within said first plane; and e) force generating means for maintaining said angular position of said second member by generating a force tending to rotate said second member within said first plane in a direction opposite to said first direction, said first force generating means generating said force in response to said rotation of said second member in said first direction, whereby said angular position of said support structure may be accurately adjusted and maintained at any angular position within said range of angular motion permitted by said rotation permitting means.

16. An apparatus for orienting a guidance device with respect to a patient's body, comprising:

a) a support structure for supporting said guidance device, said support structure having an angular position;

b) a base for said support structure, said base rotatable within a range of angular motion about first and second orthogonal axes so as to vary said angular position of said support structure, said base comprising (i) a first member, (ii) a second member rotatably mounted on said first member for rotation about said first axis, (iii) a third member rotatably mounted on said second member for rotation about said second axis, said support structure coupled to said third member;

c) a first adjusting screw for adjusting an angular position of said second member about said first axis by causing said second member to rotate in a first direction about said first axis;

d) a first spring coupled to said second member so that said rotation of said second member causes said first spring to generate a first force proportional to the magnitude of said rotation of said second member, said first force tending to rotate said second member about said first axis in a direction opposite to said first direction;

whereby said angular position of said support structure may be accurately set and maintained at varying angular positions within said range of angular motion permitted by said base.

17. The apparatus according to claim 16, further comprising:

e) a second adjusting screw for adjusting an angular position of said third member about said second axis by causing said third member to rotate in a first direction about said second axis;

f) a second spring coupled to said third member so that said rotation of said third member causes said second spring to generate a second force proportional to the magnitude of said rotation of said third member, said second force tending to rotate said third member about said second axis in a direction opposite to said first direction.

* * * * *

UNITED STATES PATENT AND TRADEMARK OFFICE
CERTIFICATE OF CORRECTION

PATENT NO. : 6,030,348
DATED : February 29, 2000
INVENTOR(S) : Evan Unger and Frederick Scott Pereles It is certified that error appears in the above-identified patent and that said Letters Patent is hereby corrected as shown below:

Column 7,
Line 42, please delete "can seen" and insert -- can be seen -- therefor.
Line 50, please delete "such magnetic" and insert -- such as magnetic -- therefor.

Signed and Sealed this

Eleventh Day of June, 2002

Attest:

JAMES E. ROGAN
Attesting Officer         Director of the United States Patent and Trademark Office